United States Patent
Brunfeld et al.

(12)
(10) Patent No.: US 6,294,793 B1
(45) Date of Patent: *Sep. 25, 2001

(54) HIGH SPEED OPTICAL INSPECTION APPARATUS FOR A TRANSPARENT DISK USING GAUSSIAN DISTRIBUTION ANALYSIS AND METHOD THEREFOR

(75) Inventors: Andrei Brunfeld, Bay-Yam; Joseph Shamir, Haifa; Gregory Toker, Jerusalem; Liviu Singher, Haifa; Ilan Laver; Ely Pekel, both of Kefau Saba, all of (IL)

(73) Assignee: Brown & Sharpe Surface Inspection Systems, Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/985,631

(22) Filed: Dec. 3, 1992

(51) Int. Cl.[7] .................................................. G01H 21/88
(52) U.S. Cl. ................................. 250/559.45; 356/239.1
(58) Field of Search .................................... 250/234–236, 250/562, 563, 571, 572, 559.45, 559.48, 559.49; 356/238, 239, 429–431, 237.2, 239.1, 237.1; 364/507; 209/588

(56) References Cited

U.S. PATENT DOCUMENTS

| 3,836,261 | * | 9/1974 | Clarke | 250/571 |
|---|---|---|---|---|
| 3,900,265 | * | 8/1975 | Merlen | 356/431 |
| 4,376,583 | * | 3/1983 | Alford et al. | 250/572 |
| 4,505,585 | * | 3/1985 | Yoshikawa et al. | 356/237 |
| 4,924,086 | * | 5/1990 | Weber | 250/235 |
| 4,954,723 | * | 9/1990 | Takahashi et al. | 250/563 |
| 5,031,112 | * | 7/1991 | Sakai et al. | 364/507 |
| 5,135,305 | * | 8/1992 | Uto et al. | 250/563 |

\* cited by examiner

Primary Examiner—Stephone B. Allen
(74) Attorney, Agent, or Firm—Wolf, Greenfield & Sacks, P.C.

(57) ABSTRACT

An optical inspection apparatus operates at high speed at very high resolution for detecting defects in transparent disks in a production environment. These transparent disks are of the type commonly used as disk platters in hard disk drives. This apparatus uses a laser beam directed to a polygon scanner, which provides a linear scan of the beam along a radius of the disk. The disk to be inspected is rotated such that its entire surface passes the scan path of the laser beam. The laser beam, after passing through the unit to be inspected, is directed to a parallel detector array, which detects changes in the nominal Gaussian distribution of the laser beam that correspond to defects in the surface of the transparent disk above a programmable threshold level. This parallel detection method allows the inspection apparatus to identify defects much smaller than the diffraction limits of the optics used, and will accurately identify changes of the laser beam caused by defects in the disk. An automatic disk handler loads untested disks into the apparatus and unloads and sorts tested disks according to the results of the inspection.

101 Claims, 10 Drawing Sheets

TRANSPARENT DISK INSPECTION SYSTEM

SURFACE INSPECTION ASSEMBLY
FOR TRANSPARENT DISKS

HIGH SPEED OPTICAL INSPECTION APPARATUS FOR A TRANSPARENT DISK USING GAUSSIAN DISTRIBUTION ANALYSIS AND METHOD THEREFOR

RELATED APPLICATIONS

This patent application is related to three other U.S. patent applications entitled: "High Speed Optical Inspection Apparatus and Method", "High Speed Optical Inspection Apparatus for a Reflective Disk and Method Therefor", and "High Speed Optical Inspection Apparatus for a Transparent Flat Panel and Method Therefor" which are assigned to the same assignee as this patent application and which are filed on the same date as the date of this patent application.

FIELD OF THE INVENTION

This invention generally relates to optical apparatus and methods, and relates, more specifically, to an optical inspection apparatus and method for detecting faults in a flat, polished transparent disk, such as those commonly used as platters for hard disk drives. This apparatus inspects with high resolution at high speed with automatic handling of the disk to allow the apparatus to be used effectively in a production inspection environment.

DESCRIPTION OF THE PRIOR ART

Disks for hard disk drives require a surface that is flat to a high degree of accuracy, and that is free from defects such as scratches and chips. Some optical inspection systems have been used with limited success in inspecting transparent disks, but do not provide the accuracy or speed that is needed in a production environment.

Dark field microscopes and scatterometers are inspection apparatus well-known in the art. A dark field microscope can somewhat accurately locate surface defects, but takes too long to inspect to be effectively used in a production environment. A scatterometer is faster than a dark field microscope, but has less accuracy (detects fewer defects). Both the dark field microscope and the scatterometer have low detection sensitivity to shallow defects or defects that are more shallow than the wavelength of the light used, which cause a phase shift in the light beam but do not diffuse (scatter) the light in different directions. An interferometer, which is well-known in the art, is suitable to detecting phase shifts, but takes substantial time and effort to set up, limiting its use to laboratory environments.

The inherent limitations of the prior art inspection systems have limited their use in industrial production environments. Indeed, the most common inspection method used in a production environment is a manual, visual inspection by human inspectors, which hold the disk in their hands and move the disk in ambient or special light looking for the presence of scratches, chips and other defects. This inspection method is labor intensive, relatively slow, and subject to human errors such as missed defects which the human eye cannot easily distinguish.

Therefore, there existed a need to provide a high speed optical inspection system and method which has a high sensitivity to defects which can be used to inspect transparent disks in a production environment. This inspection system includes automatic handling of the disks, high speed inspection, and high resolution to detect defects smaller that the spot size of the beam and/or more shallow than the wavelength of light used. The increased speed of this apparatus increases throughput of the production system, and assures that any mistakes or defects introduced by human inspectors is eliminated.

SUMMARY OF THE INVENTION

It is an object of this invention to provide a high-speed optical inspection apparatus and method suitable for production testing of transparent disks.

It is another object of this invention to provide a high speed optical inspection apparatus and method which is computer-controlled using an IBM PC-AT computer or equivalent.

It is a further object of this invention to provide a high speed optical inspection apparatus and method with surface inspection which has a high speed optical scanner to provide linear movement of the beam across a radius of the disk, and a disk actuator to rotate the disk, thereby positioning each portion of the disk in the path of the linear movement of the beam, thereby completely inspecting the entire face surface of the disk.

It is still another object of this invention to provide a high speed optical inspection apparatus and method with edge inspection using a light source and linear Charge-Coupled Device (CCD) cameras which scan the edge of the disk as it is rotated during surface inspection.

It is yet another object of this invention to provide a high speed optical inspection apparatus and method which has an automatic disk handler for automatically loading the disks into the apparatus and for automatically unloading the disks from the apparatus.

It is a still further object of this invention to provide a high speed optical inspection apparatus and method which detects both phase and amplitude changes of the light beam using multiple detectors to sense changes in the nominal Gaussian distribution of the light beam.

It is yet another object of this invention to provide a high speed optical inspection apparatus and method which has a trigger detector within the path of the scanning light beam to provide a signal to synchronize the controlling computer to the scan of the light beam.

According to the preferred embodiment of the present invention, an optical inspection apparatus for inspecting a transparent disk is provided. This inspection apparatus is controlled by an IBM PC-AT computer or equivalent, and has a typical color monitor, printer and keyboard. An Optical Inspection Assembly is provided which comprises a Surface Inspection Assembly and an Edge Inspection Assembly. The Surface Inspection Assembly nominally comprises a laser light source which transmits a light beam, a high-speed Optical Scanner, Scanning Optics, Detection Optics, and a Parallel Detector Array within a Detector. In this configuration the light beam in the Surface Inspection Assembly originates in the laser, is transmitted through a filter, and is transmitted to an aperture of the Optical Scanner, which reflects the light beam off the moving polygonal head within the Optical Scanner, causing the light beam to sweep across the Scanning Optics. The Scanning Optics make the light beam normal to the surface of the disk and focused at the center of the transparent disk media. On the opposite side of the disk, Detection Optics collimate the light beam and project it onto the Parallel Detector Array within the Detector. This array is typically a matrix of photodiodes or Charge-Coupled Devices (CCDs) upon which the light beam is projected. This matrix configuration provides a two dimensional Gaussian response with respect to light intensity (amplitude). Any defect in the disk deflects light from the Parallel Detector Array (causing a change in the nominal light level) or shifts its phase (causing a change in the Gaussian distribution), both of which are detected by the processing electronics coupled to the Parallel Detector Array. Thus the processing electronics simply look for changes in the nominal level or distribution of the Gaussian response provided by the Parallel Detector Array in response to a nominal light beam, which changes correspond to surface defects in the transparent disk. Once the Optical Scanner beam completes one complete linear scan, the disk is then rotated to the next position, and the scanning continues in like manner until the entire surface of the disk has been inspected. The computer controls the rotation of the disk to assure the entire surface is scanned. At the same time the disk is rotating, the Edge Inspection Assembly simultaneously inspects both the inner and outer edges of the disk for defects above a programmable threshold. If either the Surface Inspection Assembly or the Edge Inspection Assembly detects a defect greater than their programmed thresholds, a fault signal is sent to the computer to indicate that the disk failed the inspection. The Automatic Disk Handler then sorts the tested disks according to the pass or fail results of the inspection.

The foregoing and other objects, features and advantages will be apparent from the following description of the preferred embodiments of the invention as illustrated in the accompanying drawings.

BRIEF DESCRIPTION OF THE DRAWINGS

FIG. 3 is a perspective view of the Optical Inspection Assembly shown in FIG. 1a.

DESCRIPTION OF THE PREFERRED EMBODIMENT

Figure 1:
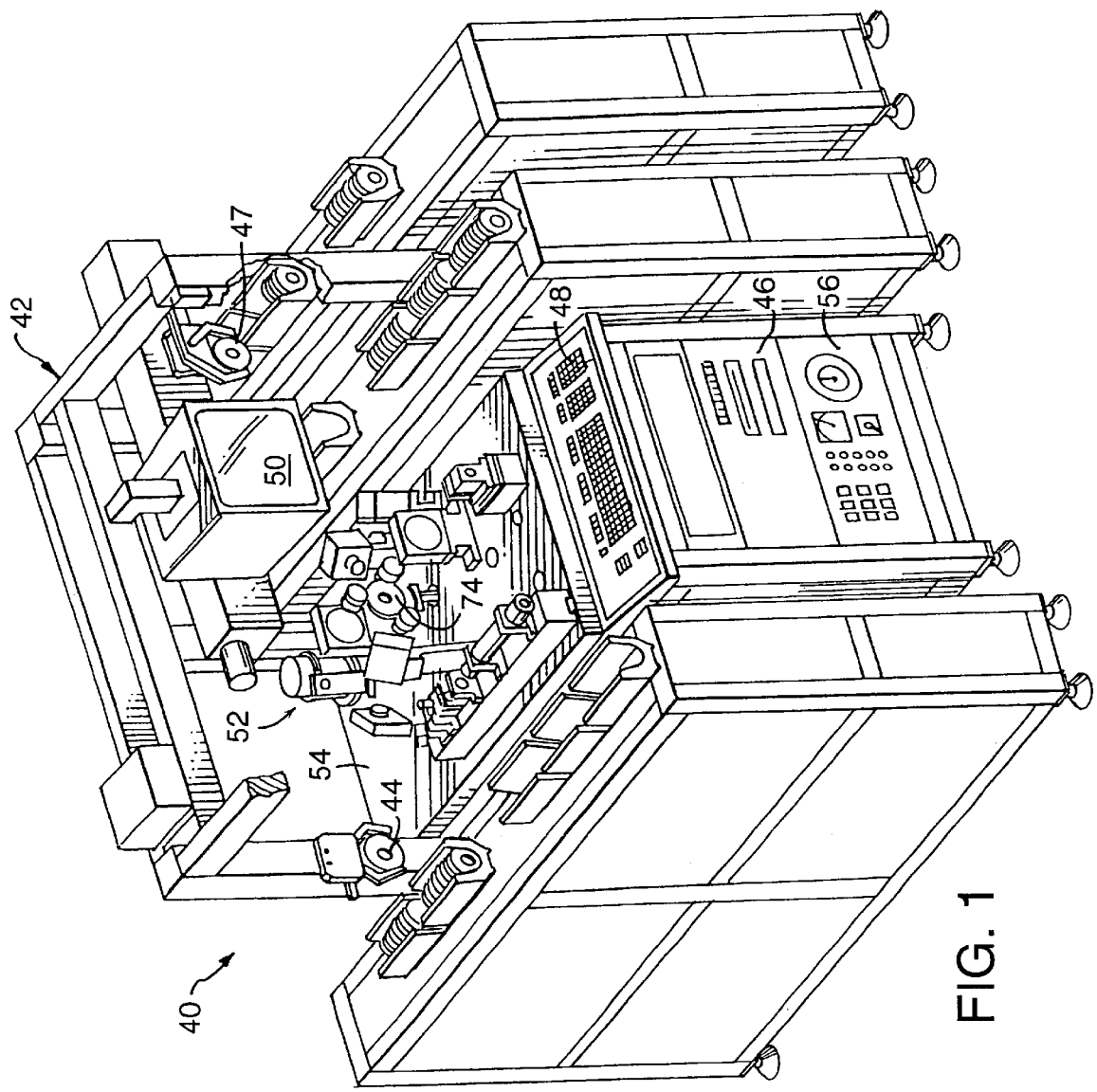
FIG. 1 is a perspective view of the optical inspection apparatus of the present invention.
Figure 1A:
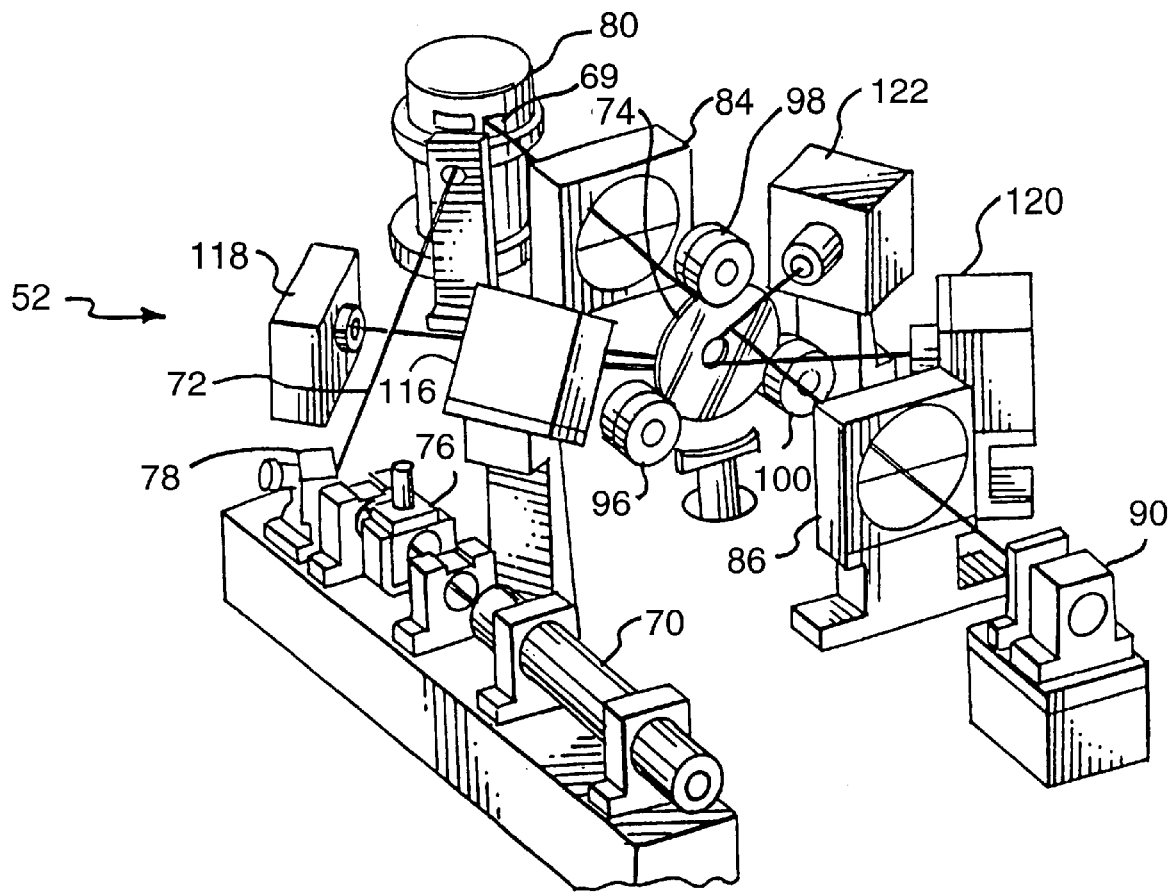
FIG. 1a is an enlarged view of the Optical Inspection Assembly shown in FIG. 1.
Figure 2:
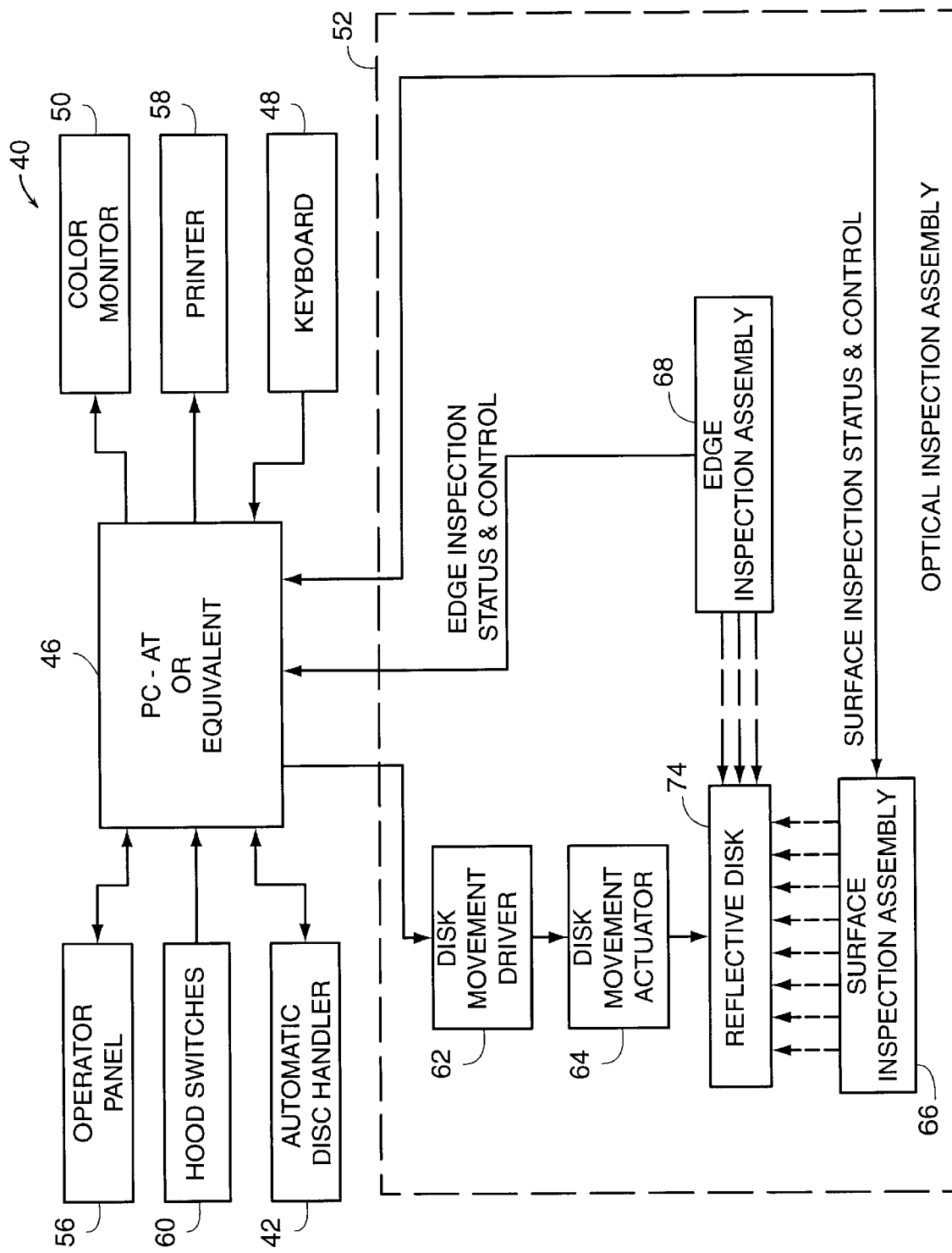
FIG. 2 is a block diagram of the optical inspection apparatus of FIG. 1.

FIG. 1 shows the optical inspection apparatus 40 of the present invention, comprising an IBM compatible PC-AT computer 46 or equivalent, a keyboard 48, a color monitor 50, an operator panel 56, an Optical Inspection Assembly 52 located on table 54, and an Automatic Disk Handler 42 (typically a robot) to automatically load and unload the disk to be inspected (44, 74, and 47) into the Optical Inspection Assembly 52. FIG. 1a is an enlarged view of the Optical Inspection Assembly 52 of FIG. 1. FIG. 2 is the block diagram of the apparatus 40 of the present invention, with numbers that correspond to numbers in FIG. 1 representing the same components. The apparatus shown in FIG. 2 includes a printer 58, and hood switches 60 for detecting when the apparatus 40 is ready for operation. These hood switches 60 act as safety devices, inhibiting operation of the apparatus 40 until the apparatus 40 is in the correct configuration with all hoods secured properly. The Optical Inspection Assembly 52 comprises a Disk Movement Driver 62, a Disk Movement Actuator 64, a Surface Inspection Assembly 66, an Edge Inspection Assembly 68, and a Transparent Disk 74.

The Automatic Disk Handler 42 first loads the Transparent Disk 74 into the Optical Inspection Assembly 52. The Surface Inspection Assembly 66 then begins its scan of the surface of the Transparent Disk 74. At the same time the Edge Inspection Assembly 68 begins inspection of the inner and outer edges of the Transparent Disk 74. Both the Surface Inspection Assembly 66 and the Edge Inspection Assembly 68 perform only a linear inspection, and thus depend on the Disk Movement Actuator 64 to rotate the Transparent Disk 74 such that the entire surface is inspected by the Surface Inspection Assembly 66, and such that the entire edge is inspected by the Edge Inspection Assembly 68.

The Surface Inspection Assembly 66 and the Edge Inspection Assembly 68 both have programmable thresholds that determine the characteristics of allowable defects. If either of these assemblies detects a defect greater than the programmed threshold, a fault signal is sent to the computer 46 to indicate that the inspection failed. The computer 46 causes the Automatic Disk Handler 42 to place good disks (those that pass inspection) in one place, and to place bad disks (those that fail inspection) in a different place. In a fully automated system, an automated cart or conveyer would deliver uninspected disks and take away both good and bad inspected disks as the apparatus 40 requires.

Figure 3:
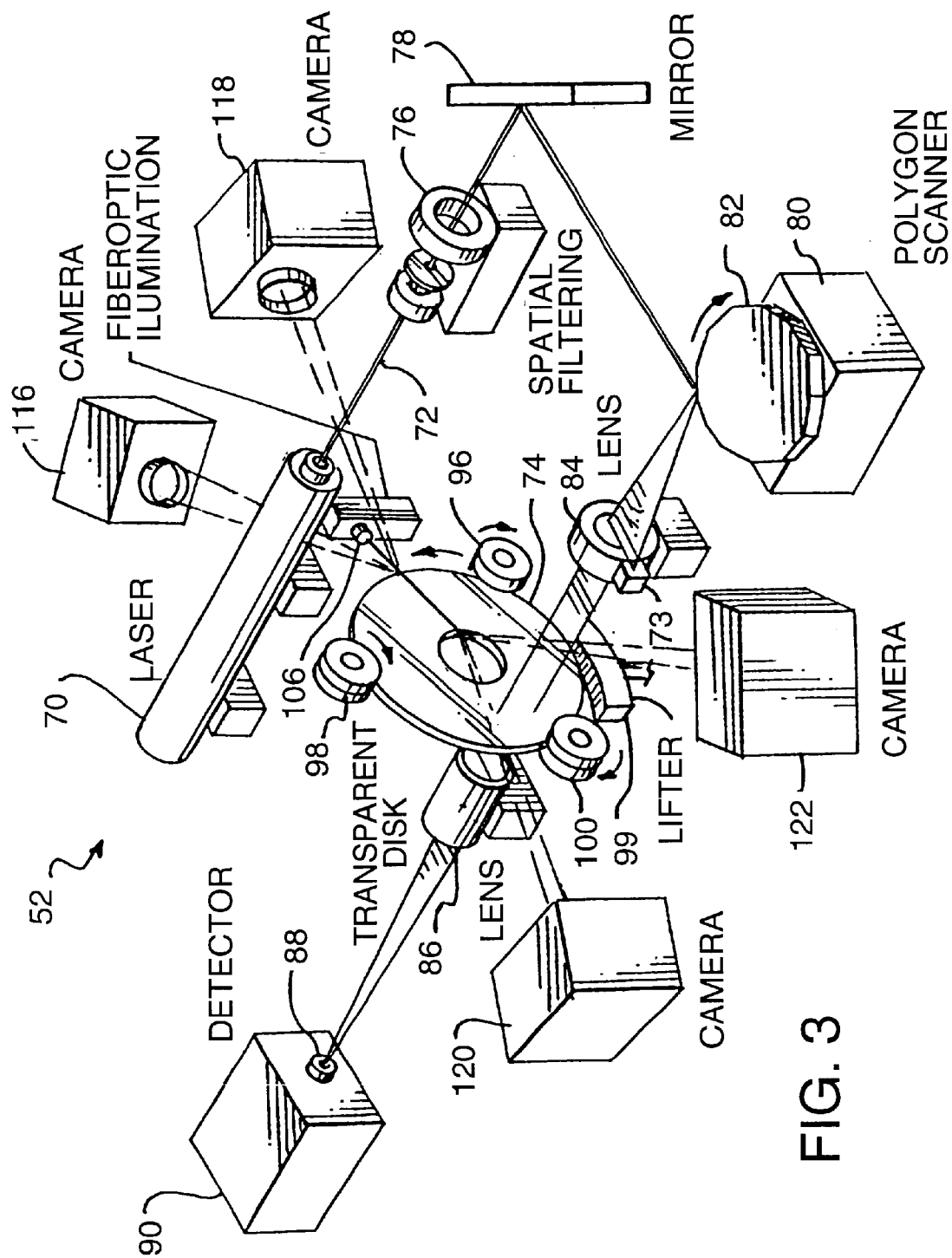

The Optical Inspection Assembly 52 is shown in FIG. 3. A laser 70 provides the light beam 72 used to inspect the Transparent Disk 74. The laser 70 must have a minimum spatial and temporal coherence greater than the defects to be measured. The coherence of the laser 70 is related to its optical Signal to Noise (S/N) ratio, while the power of the laser 70 is related to its electrical S/N ratio. The light beam 72 passes through Filter Optics 76, which increases the spatial coherence of the beam 72 and shapes and directs the beam 72 to the mirror 78, which directs the beam 72 to an aperture 69 on Optical Scanner 80. The aperture 69 on Optical Scanner 80 is shown in FIG. 1*a*. Referring again to FIG. 3, Optical Scanner 80 has a rotating polygonal head 82 with reflective faces. The beam 72 passes through the aperture (not shown in FIG. 3) onto the rotating polygonal head 82, which causes the beam 72 to sweep across the Scanning Optics 84. If the polygonal head 82 rotates clockwise as shown, the sweep of the beam 72 will be from left to right on the Transparent Disk 74.

The Scanning Optics 84 are placed at the precise distance from the polygonal head 82 of Optical Scanner 80 defined by the focal length of the Scanning Optics 84. The Transparent Disk 74 is placed at this same distance from the Scanning Optics 84, such that the focal point of the beam 72 is at the exact center of Transparent Disk 74. After passing through the focal point in the center of Transparent Disk 74, the beam 72 diverges and contacts Detection Optics 86, which is placed at a distance from the Transparent Disk 74 that corresponds to its focal length. The Detection Optics 86 cause each point along the beam scan to project on the Parallel Detector Array 88 within Detector 90, which is also placed at a distance from the Detection Optics 86 that corresponds to the focal length of Detection Optics 86.

Figure 9A:
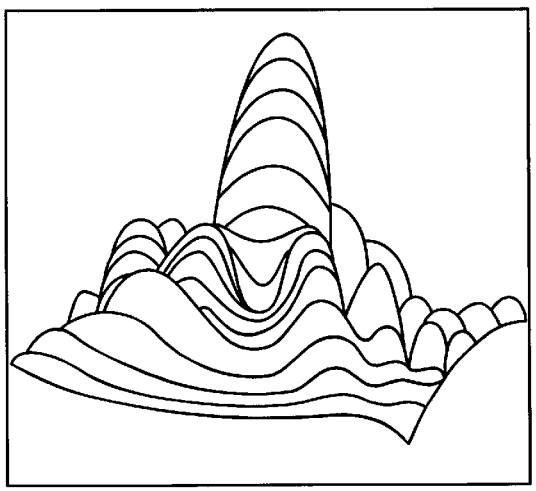
FIG. 9a is a three dimensional representation of a typical Gaussian distribution of light intensity (amplitude).
Figure 9B:
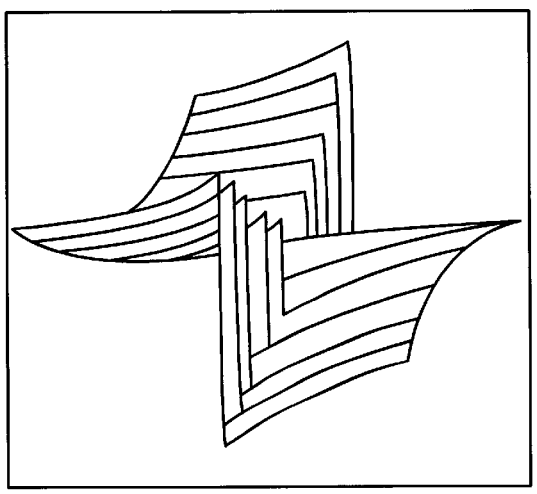
FIG. 9b is a three dimensional representation of a typical Gaussian distribution of light phase.
Figure 11:
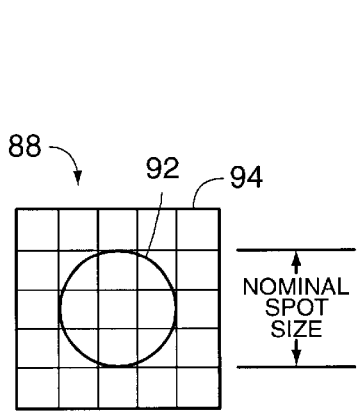
FIG. 11 is a front view of one specific configuration of the Parallel Detector Array which detects changes in the amplitude and/or phase of the Optical Scanner beam.

One specific implementation of the Parallel Detector Array 88 is shown in FIG. 11. An array of light sensitive devices 94 is provided, typically a photodiode array. Each light sensitive device 94 provides an electrical signal proportional to the intensity of light it detects. A nominal beam spot 92 is shown, which is smaller than the matrix as shown. This type of a spot 92 of laser light on Parallel Detector Array 88 causes a two-dimensional response with respect to intensity or amplitude, which is represented in FIG. 9*a*. Likewise, this type of spot 92 causes a two-dimensional response with respect to changes of phase, which is represented in FIG. 9*b*. The changes of phase will create an interference pattern between the center and outer rim of the beam 72, causing a change in the ideal Gaussian distribution.

Figure 11B:
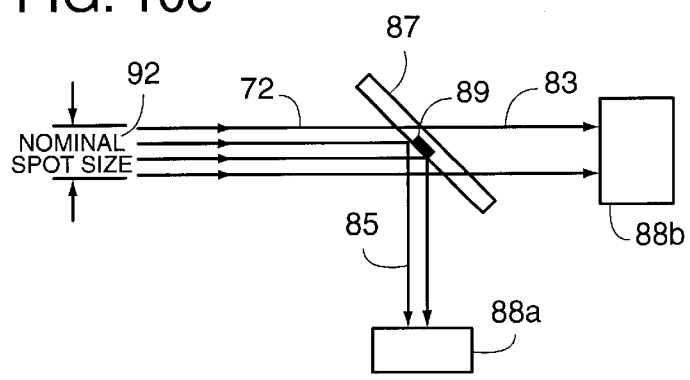
FIG. 11b is a top view of the optics function of an alternative parallel detection configuration which detects changes in the amplitude and/or phase of the Optical Scanner beam.
Figure 11A:
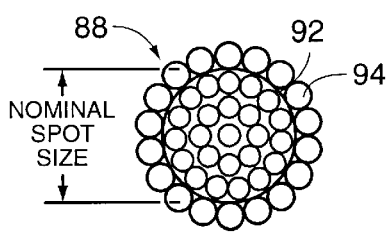
FIG. 11a is a front view of another specific configuration of the Parallel Detector Array which detects changes in the amplitude and/or phase of the Optical Scanner beam.
Figure 11C:
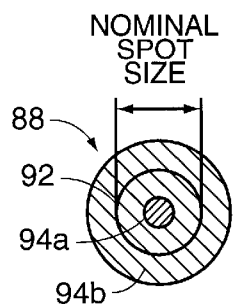
FIG. 11c is a front view of another specific configuration of the Parallel Detector Array which detects changes in the amplitude and/or phase of the Optical Scanner beam.

Note that the light sensitive devices 94 of Parallel Detector Array 88 could also be an array of CCDs, and could be arranged in any physical configuration, such as circular or concentric rings of individual detectors, as shown in FIG. 11*a*. In addition, two concentric ring detectors in the configuration shown in FIG. 11*c* could be used to form Parallel Detector Array 88. Detector 94*a* detects the center portion of the beam, while detector 94*b* detects the outer portion of the beam, which has nominal spot size 92 as shown.

FIG. 11*b* shows an alternative arrangement which uses two Parallel Detector Arrays 88. Beam 72 has a nominal spot size 92 as shown. Beam 72 is projected onto a transparent substrate 87 which has a small reflective portion 89, and is positioned at a 45 degree angle with respect to the beam 72 as shown. In this manner the center portion 85 of beam 72 is reflected off the reflective portion 89 of transparent substrate 87 to a Parallel Detector Array 88*a* as shown in the figure. The outer portion 83 of the beam 72 passes through the transparent substrate 87 onto a second Parallel Detector Array 88*b*. In this manner the two Parallel Detector Arrays 88*a* and 88*b* act in parallel to detect any change in the nominal Gaussian distribution of light within beam 72.

Note that the Parallel Detector Arrays 88*a* and 88*b* shown in FIG. 11*b* could be replaced with a single detector, since the two detectors 88*a* and 88*b* act in parallel, and can therefore detect with only two sensors changes in the nominal Gaussian distribution of the beam 72. Neither the number, type of device used nor the physical arrangement of these devices is critical to this invention. The primary inventive feature regarding the Parallel Detector Array 88 is the use of more than one optical detector in parallel to detect changes in a nominally Gaussian distribution of light within the spot of the optical beam 72.

By measuring changes in the Gaussian distribution of light, the apparatus 40 of the present invention has a much higher resolution than prior art optical inspection systems, which are limited by the diffraction limits of the optics and specific configuration of the system. By measuring changes in the Gaussian distribution of the beam 72, the apparatus 40 measures changes in the electromagnetic fields in a general point in space, which therefore removes the classical diffraction limit experienced by prior art systems. Since the Parallel Detector Array 88 can detect changes in both phase and amplitude of the nominal Gaussian distribution of light (phase changes are detected by interference between the center and rim of the beam), a change in the surface characteristics caused by even a very narrow or shallow defect will interfere with the rest of the field, and will be detected. This allows the lateral resolution of the apparatus 40 to be from 100 to 1000 times greater than the diffraction limit, since phase changes are detected as well as amplitude changes. In addition, the longitudinal sensitivity within the diffraction limit is interferometric, while the adjustment sensitivity is only dependent on the depth of field. These features provide for a highly sensitive inspection apparatus 40, which can detect any changes of the optical characteristics of the inspected surface on the order of $\frac{1}{100}$ to $\frac{1}{1000}$ of the diffraction limit in all three axes.

Referring again to FIG. 3, rollers 96, 98 and 100 comprise the Disk Movement Actuator 64 shown in FIG. 2. Only one of these three rollers 96, 98 and 100 are motor-driven, with the computer 46 controlling the motor drive through communicating with the Disk Movement Driver 62 as shown in FIG. 2. For illustration purposes, it will be assumed that roller 96 is the one roller that is driven by a motor, and that it rotates in a clockwise direction as shown. As the Optical Scanner 80 sweeps the beam 72 repeatedly from left to right on a radius of Transparent Disk 74, the computer 46 causes roller 96 to rotate clockwise, which causes Transparent Disk 74 to rotate counter-clockwise. In this manner the entire surface of Transparent Disk 74 is scanned when it has rotated one revolution.

Figure 10A:
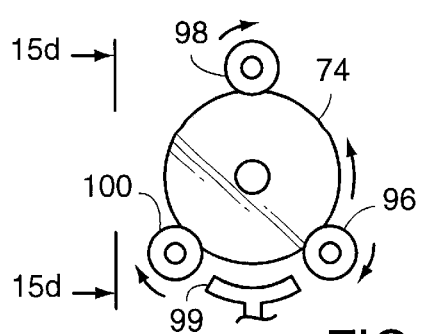
FIG. 10a is an elevational view of the disk of FIG. 3 showing the roller configuration which rotates the disk during inspection.
Figure 10B:
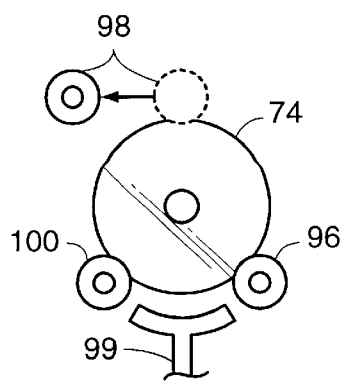
FIG. 10b is an elevational view of the disk and rollers of FIG. 10a showing how the top roller moves to facilitate loading and unloading of the disk by the Automatic Disk Handler.
Figure 10C:
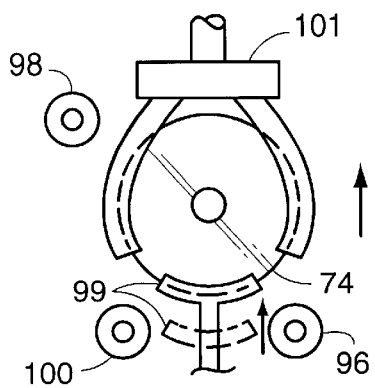
FIG. 10c is an elevational view of the disk and rollers of FIG. 10b showing how the movement of the roller shown in FIG. 10b and the operation of the lifter allow the Automatic Disk Handler to load and unload the disk into the apparatus of FIG. 3.
Figure 10D:
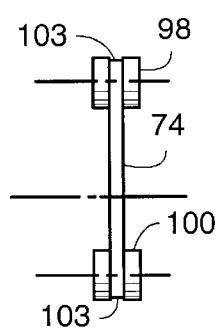
FIG. 10d is a side view of two of the rollers and the disk shown in FIG. 10a taken along the line 10d—10d showing the slot in the rollers for holding the disk in place during rotation.

FIG. 3 shows a lifter 99, which acts in conjunction with the Automatic Disk Handler 42 (not shown) to load untested disks into the Optical Inspection Assembly 52 and to unload tested disks from the Optical Inspection Assembly 52. The detailed operation of the loading and unloading function can be best understood in reference to FIG. 10a–c. These three figures illustrate how the Transparent Disk 74 is unloaded from the Optical Inspection Assembly 52 by the Gripping Arm 101 of the Automatic Disk Handler 42. FIG. 10a shows a Transparent Disk 74 while it is being rotated under test by rollers 96, 98 and 100. Lifter 99 is positioned away from the Transparent Disk 74 during testing. When testing is complete, the computer 46 stops driving roller 96, causing the rotation of the rollers 96, 98 and 100 to stop. The computer 46 then moves the roller 98 out of the way as shown in FIG. 10b. Once roller 98 is out of the way, the Gripping Arm 101 of Automatic Disk Handler 42 is placed into the proper position, and lifter 99 then lifts the Transparent Disk 74 away from rollers 96 and 98, to a position where Gripping Arm 101 can close and thereby grip the Transparent Disk 74, as shown in FIG. 10c. This process is reversed for loading disks into the Optical Inspection Assembly 52. FIG. 10d shows a side view of the rollers 98 and 100 and the Transparent Disk 74 shown in FIG. 10a, illustrating the narrow slots or "V" grooves 103 used to hold the Transparent Disk 74 in the proper position on the rollers 96, 98 and 100.

Figure 4:
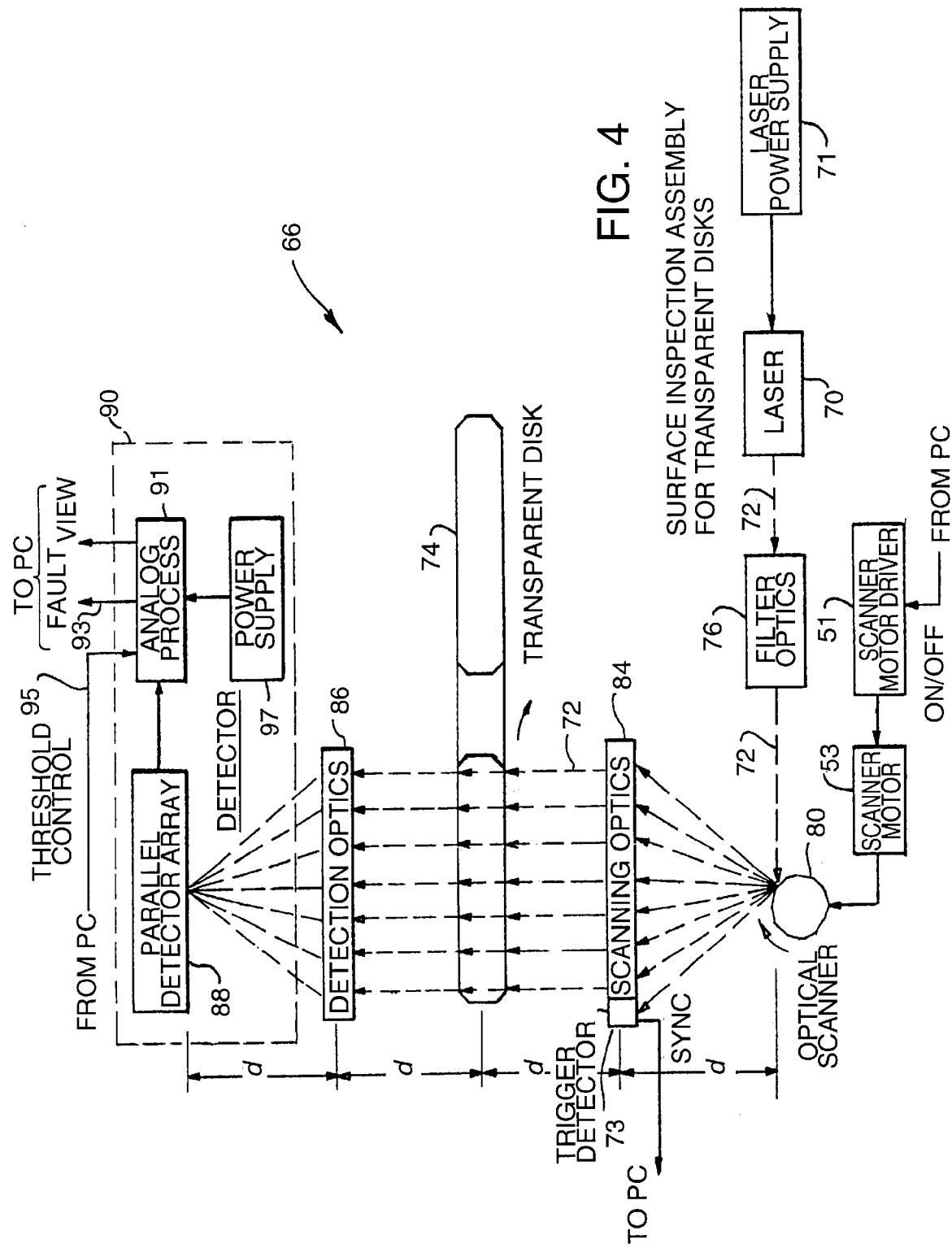
FIG. 4 is a block diagram of the Surface Inspection Assembly portion of the Optical Inspection Assembly shown in FIG. 3.

FIG. 4 shows the configuration of the Surface Inspection Assembly 66 shown in FIG. 2 used in the Optical Inspection Assembly 52. Note that many of the numbers in FIG. 4 correspond to components shown in FIG. 3. The laser 70 is powered by a Laser Power Supply 71, and provides beam 72, which passes through Filter Optics 76. The mirror 78 of FIG. 3 is not shown in FIG. 4. The light beam 72 contacts the Optical Scanner 80, which provides a linear scanning action of the beam 72 across Trigger Detector 73 and Scanning Optics 84. Trigger Detector 73 is placed at the beginning position of the scan path of beam 72, and provides an electrical SYNC signal to the computer 46 when the beam 72 contacts it to synchronize the sweep of beam 72 with the rotation of the Transparent Disk 74 and the output of Detector 90. Note that the Optical Scanner 80 can be switched on or off by the computer 46 giving the appropriate command to the Scanner Motor Driver 51, which controls the Scanner Motor 53. Also note that the Trigger Detector 73 can be mounted anywhere within the scan path of beam 72. In the configuration illustrated in the figures, Trigger Detector 73 is mounted on the side of the Scanning Optics 84. The Trigger Detector 73 could, in the alternative, be placed in the scan path of beam 72 next to the Transparent Disk 74. By placing the Trigger Detector 73 next to the Scanning Optics 84, no optic field of Scanning Optics 84 is taken by Trigger Detector 73.

As shown in FIG. 4, the angle sweep of Optical Scanner 80 is converted by the Scanning Optics 84 to a sweep of parallel beams, each contacting the Transparent Disk 74 normal to its surface. The beam 72 continues through the Transparent Disk 74 to Detection Optics 86, which directs each beam to the Parallel Detector Array 88 within Detector 90. The nominal Gaussian output of Parallel Detector Array 88 is processed by analog circuitry in the Analog Process block 91, which is powered by Power Supply 97. Analog Process 91 receives a threshold control signal 95 from the computer 46 and detects any change in the Gaussian distribution of beam 72 which corresponds to a defect greater than the programmed threshold. When such a defect occurs, the Analog Process 91 signals the computer 46 that the inspection failed by asserting a Fault signal 93. The computer 46 will then nominally abort the inspection of the Transparent Disk 74, and cause the failed disk to be placed in the area of bad disks by the Automatic Disk Handler 42.

Figure 5:
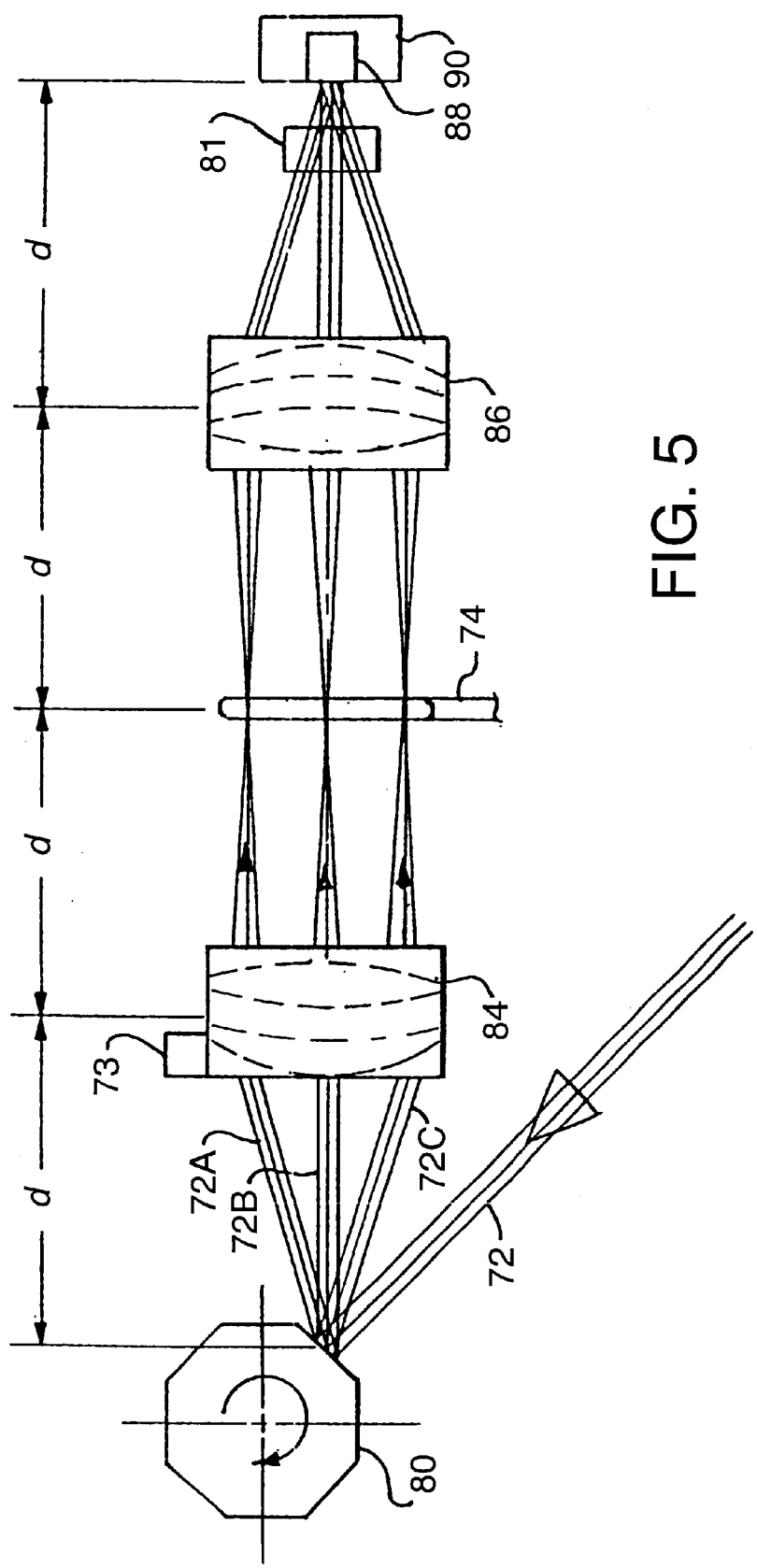
FIG. 5 is a top view of the Optical Scanner and optics function in the Surface Inspection Assembly shown in FIG. 4 for transparent disks.

FIG. 5 clearly represents the operation of the Scanning Optics 84 and the Detection Optics 86. With the configuration as previously described, the beam 72 is reflected off the Optical Scanner 80, and first contacts the Trigger Detector 73, then continues to scan across the Scanning Optics 84. Beam 72 first comes in contact with Scanning Optics 84 on the left side of the Scanning Optics 84, as represented by 72A in FIG. 5. Scanning Optics 84 focuses the beam to a small spot at the exact center of the Transparent Disk 74 as shown. After passing through the focal point at the center of the Transparent Disk 74, the beam 72A begins to diverge. The beam 72A then contacts Detection Optics 86, which directs the beam 72A to the Parallel Detector Array 88 within Detector 90. Note that Optional Detection Optics 81 may be used to magnify the beam 72, to correct for wandering of beam 72, or for other purposes as required.

As the Optical Scanner beam 72 continues its sweep, it will come to the position shown by 72B, and eventually to the position shown by 72C. Note that for each position of the beam 72, a different spot on the Transparent Disk 74 is in the path of the beam 72, and the resulting beam is projected onto the Parallel Detector Array 88 as shown. Note that this method can only be accomplished by placing the Optical Scanner 80 at a distance d from Scanning optics 84 equal to the focal length of Scanning Optics 84. The center of the Transparent Disk 74 is located at this same distance from the Scanning Optics 84. In like manner, Detection Optics 86 is located this same distance from the center of the Transparent Disk 74, and the Parallel Detector Array 88 is located this same distance from the Detection Optics 86. In this configuration the size of the beam 72 at the Optical Scanner 80 is nominally the same size as the beam 72 at the Parallel Detector Array 88.

As the scanning of beam 72 takes place along a linear radius of the Transparent Disk 74, the Transparent Disk 74 is rotated one complete revolution to assure the entire disk surface is inspected. While this rotation of the disk takes place, both the inner and the outer edges of the disk are inspected for defects using the Edge Inspection Assembly 68, shown in detail in FIG. 6. The Edge Inspection Assembly 68 is comprised of an Outer Radius Inspection Assembly 128 and an Inner Radius Inspection Assembly 130. Within Outer Radius Inspection Assembly 128, a Power Supply 102 powers a light source 104, which passes through Projection Optics 106 to the outer edge of the Transparent Disk 74 as shown. Each disk nominally has two beveled edges 108 and 110 and a flat edge 109 on its outer edge as shown, and two beveled edges 112 and 114 and a flat edge 113 on its inner edge as shown. As shown in the figure, beveled edge 108 and half of flat edge 109 are inspected by Detector Optics #1 116, beveled edge 110 and the other half of flat edge 109 are inspected by Detector Optics #2 118, beveled edge 112 and flat edge 113 are inspected by Detector Optics #3 120, and beveled edge 114 and the other half of flat edge 113 is inspected by Detector Optics #4 122. Detector Optics #1 116 and Detector Optics #2 118 project the image of the edge to be inspected onto detectors, the outputs of which are processed to determine if any defects occur greater than a programmable threshold. This detection and process step is represented by the Detectors and Process block 124. Likewise Detector Optics #3 120 and Detector Optics #4 122 go to a Detectors and Process block 126. Any defect in either the Outer Radius Inspection Assembly 128 or the Inner Radius Inspection Assembly 130 above their respective programmable thresholds is reported to the computer 46 as a fault, which causes the disk inspection to fail.

Figure 6:
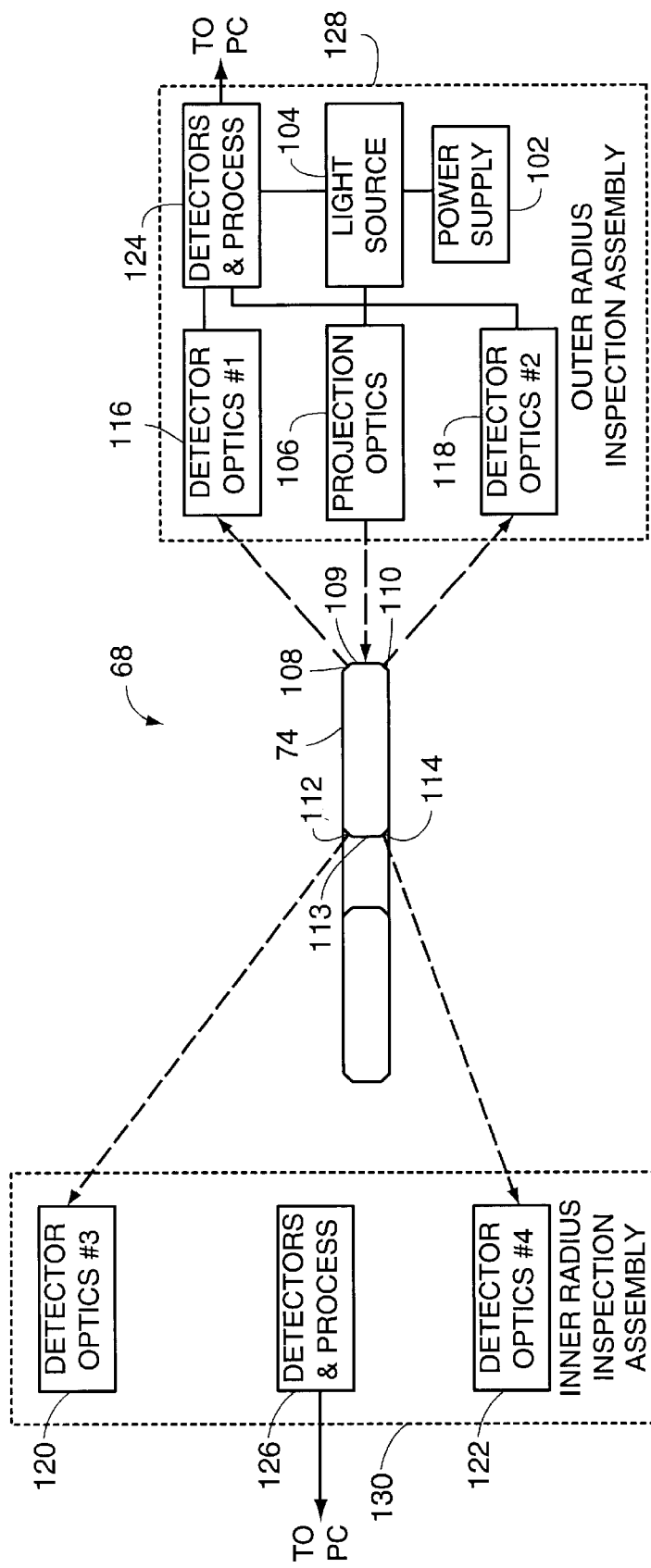
FIG. 6 is a block diagram of the Edge Inspection Assembly portion of the Optical Inspection Assembly shown in FIG. 3.
Figure 6A:
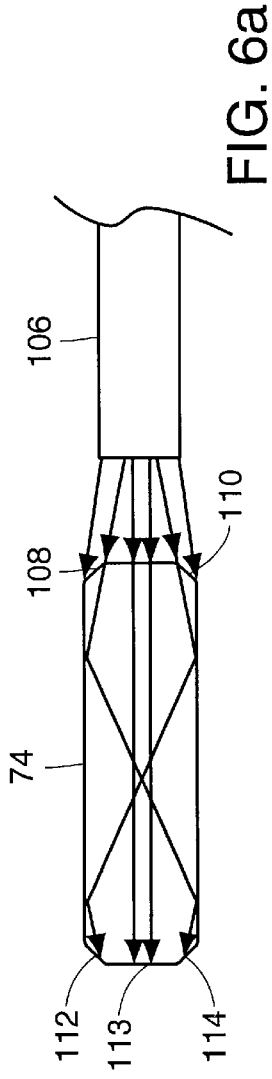
FIG. 6a is a cross-sectional view of the transparent disk shown in FIG. 6 showing how the waveguide properties of the transparent disk cause illumination of the inner edges with a light source shining on the outer edge.

FIG. 6a illustrates how the single light source 104 within the Outer Radius Inspection Assembly 128 can be used to illuminate both the outer edges (108, 109 and 110) and the inner edges (112, 113 and 114) of the Transparent Disk 74 simultaneously. The light source shines through Projection Optics 106, which illuminates the outer edge of the Transparent Disk 74 as shown. Due to the transparency of Transparent Disk 74, the light that shines onto the outer edge of the Transparent Disk 74 is transmitted through the transparent disk medium to the inner edges 112, 113 and 114. FIG. 6a shows how the Transparent Disk 74 acts as a wave guide, directing the transmitted light to the inner edges of the disk. This feature allows for simultaneous illumination and inspection of both the inner edges (112, 113 and 114) and the outer edges (108, 109 and 110) with only one light source. This is significant since the addition of a second light source to inspect the inner edges would add to the expense and complexity of the apparatus 40, since this second light source would have to be positioned after the Transparent Disk 74 is loaded for testing, and removed prior to the Transparent Disk 74 being unloaded after testing.

Figure 7:
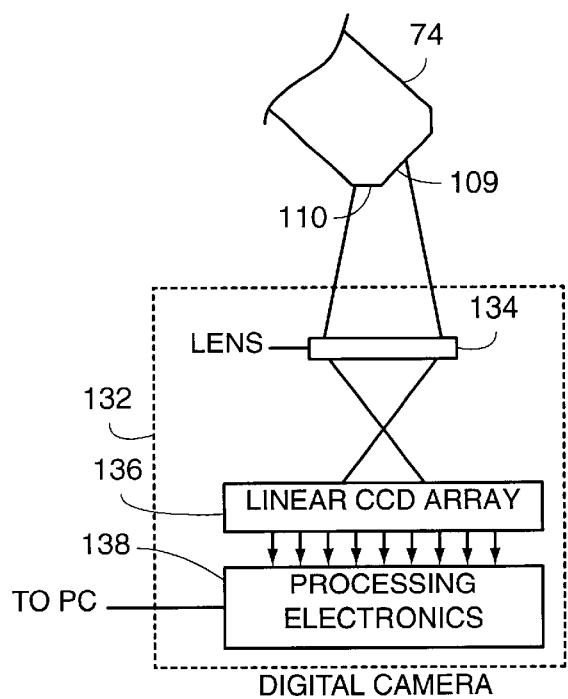
FIG. 7 is a partial perspective view of one particular implementation of the outer radius inspection assembly shown in FIG. 6 using a camera having a linear CCD array.

Many of the components shown in FIG. 6 are also represented in FIG. 3 in their preferred configurations of the present invention. Projection Optics 106 is a fiberoptic strand as represented in FIG. 3. Each of the Detector Optics 116, 118, 120 and 122 are digital CCD cameras in the first embodiment shown in FIG. 3. A detailed view of the operation of one of the digital CCD cameras is shown in FIG. 7. For illustrative purposes, inspection of edge 110 and half of edge 109 of the Transparent Disk 74 is shown. The digital CCD camera 132 has a single row of CCDS, known as a Linear CCD Array 136. The image of the edge 110 and the half of edge 109 of the Transparent Disk 74 to be inspected is focused by the lens 134 of the camera 132 onto the Linear CCD Array 136 as shown. The Processing Electronics 138 then processes the outputs from the Linear CCD Array 136 and asserts a fault signal to the computer 46 if a defect above a programmable threshold value exists. The Linear CCD Array 136 only detects a small portion of the edges as shown in FIG. 7, but the rotation of the disk for one revolution during inspection allows the camera 132 to inspect the entire edge during that one revolution. This occurs simultaneously for all edges 108, 109, 110, 112, 113 and 114 shown in FIG. 6, and occurs simultaneously with the inspection of the surface of the Transparent Disk 74 by the Surface Inspection Assembly 66.

Each inspection assembly in the apparatus 40 of the present invention has its own programmable threshold above which a fault will be signaled, causing the disk inspection to fail. In this manner the computer 46 only has to load the disk, rotate the disk, and monitor the outputs of each inspection assembly for faults. If a fault is signaled to the computer 46 prior to a full revolution being completed, the inspection fails and the disk is unloaded by the Automatic Disk Handler 42 and placed in the place for "bad" disks. If the computer 46 completes a full rotation of the disk with no fault signal from any of the inspection assemblies, the disk passes the inspection and is unloaded by the Automatic Disk Handler 42 and placed in the place for "good" disks.

Figure 8A:
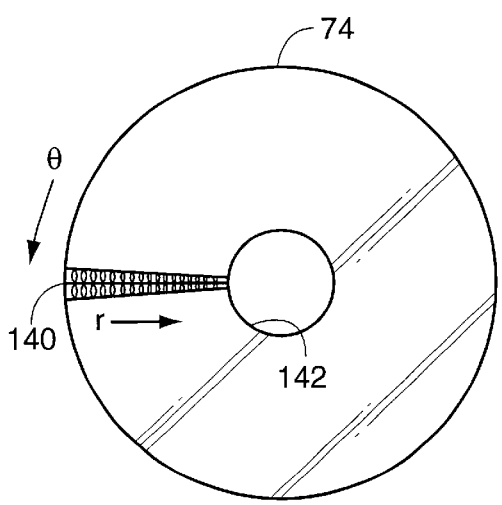
FIG. 8a is a front view of the transparent disk shown in FIG. 3 showing the scanning in the r direction, and rotation of the disk in the theta direction.
Figure 8B:
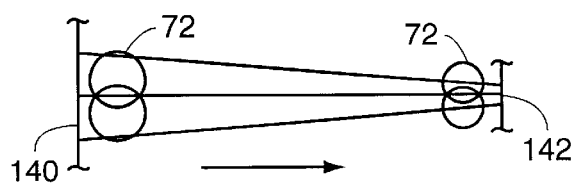
FIG. 8b is an enlarged view of the scanned portion of FIG. 8a showing how the combination of the linear travel of the beam and the rotation of the disk results in complete scanning of the entire surface of the disk.

FIG. 8a and 8b illustrate how the combination of the scanning of the beam 72 and the rotation of the Transparent Disk 74 provide for a complete inspection of the entire surface of the Transparent Disk 74. As shown in FIG. 8a, the beam 72 scans in a line from left to right as shown by the r direction. At the same time the disk rotates in the theta direction shown in the figure. In this manner the disk is inspected in polar coordinates, with the r coordinate representing the position of the beam 72 in its scan path, and the theta coordinate representing the rotational position of the Transparent Disk 74. The effect of this polar scanning technique is shown in FIG. 8b.

The beam is configured to scan along a radius of the Transparent Disk 74, from left to right as shown. The beam has a spot size which travels along this scan path. In order for the beam 72 to completely scan the entire surface of the Transparent Disk 74, the beam 72 must overlap somewhat with the previous scan path. Due to the circular configuration of the disk the outside circumference is significantly greater than the inside circumference, so a rotational change of position causes the outer edge to travel a farther distance than the inner edge. This means that the spot must overlap slightly on the outer edge 140 of the disk, which causes a much greater overlap on the inner edge 142 of the disk, as shown in FIG. 10b. This difference in overlap between the beam at the outer edge 140 and the inner edge 142 of the Transparent Disk 74 can be corrected using electronics or software to provide for accurate mapping of disk defects.

Figure 12:
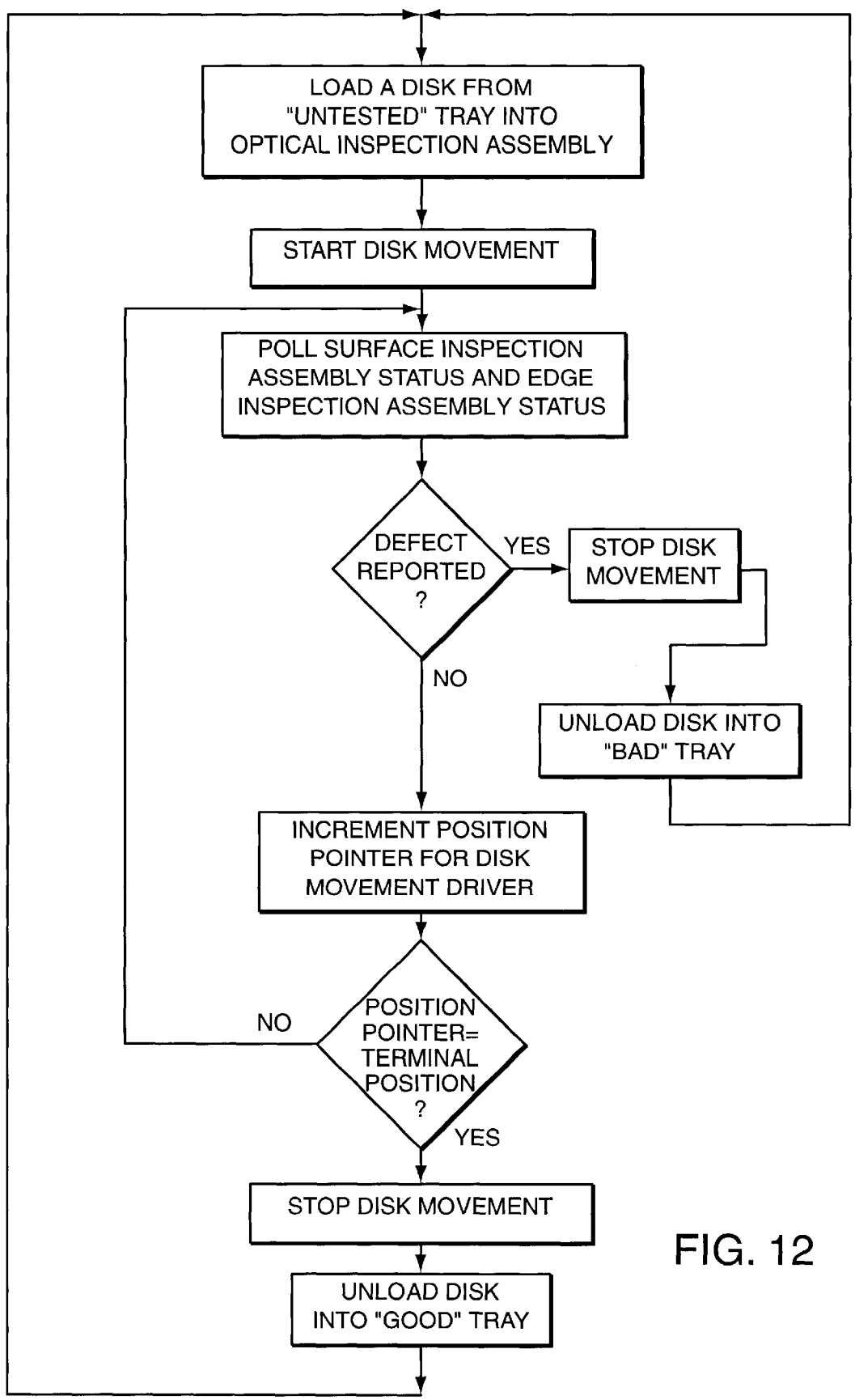
FIG. 12 is a flow chart of the control software operation for the apparatus of the present invention.

The flow chart of the program flow of the control software within computer 46 is shown in FIG. 12. The specific implementation shown in FIG. 12 assumes that the computer 46 will poll the Surface Inspection Assembly 66 and the Edge Inspection Assembly 68 to determine whether a defect is reported by either of these assemblies. In an alternative arrangement, the fault output 93 of the Surface Inspection Assembly 66 and the fault output 93 of the Edge Inspection Assembly 68 are interrupt-driven inputs to computer 46, which report a fault by interrupting program execution of the computer 46. In this configuration the computer 46 simply completes the rotation of the disk, then checks a software flag to determine whether a fault was detected during the scan.

The automation of apparatus 40 provided by computer 46 and Automatic Disk Handler 42 provides for high-speed inspection of apparatus 40, which suits the apparatus 40 well to a speed sensitive production environment.

While the invention has been described in its preferred embodiments, it is to be understood that the words which have been used are words of description rather than limitation, and that changes may be made within the purview of the appended claims without departing from the true scope and spirit of the invention in its broader aspects.

What is claimed is:

1. An optical inspection apparatus for inspecting flat, transparent circular disk comprising, in combination:
   computer means for controlling said apparatus;
   operator interface means coupled to said computer means for providing input data from an operator to said computer means and for providing output data from said computer means to said operator;
   an optical inspection assembly, coupled to said computer means having output means for reporting to said computer means results of an inspection performed by said optical inspection assembly, comprising inspection means consisting of detector means for detecting changes of a normal Gaussian distribution of a light beam passing through a transparent disk; and
   said transparent disk which is placed in said optical inspection assembly to inspect said transparent disk for defects.

2. The apparatus of claim 1 further comprising automatic disk handler means coupled to said computer means for loading under control of said computer means said transparent disk into said optical inspection assembly and for unloading under control of said computer means said transparent disk out of said optical inspection assembly.

3. The apparatus of claim 1 wherein said computer means comprising, in combination:

an IBM compatible personal computer; and control software means loaded into memory of said IBM compatible personal computer for determining function and sequence of operations of said apparatus.

4. The apparatus of claim 3 wherein said control software means comprising:

a main control program; and a plurality of device drivers which provide subroutines for said main control program and which control individual components of said apparatus.

5. The apparatus of claim 1 wherein said computer means periodically polls said output means of said optical inspection assembly to determine whether a defect has been detected by said optical inspection assembly.

6. The apparatus of claim 1 wherein said output means of said optical inspection means is coupled to said computer means such that said output means interrupts said computer means when a defect is detected by said optical inspection assembly.

7. The apparatus of claim 1 wherein said operator interface means comprising, in combination:

keyboard means coupled to said computer means for providing said input data from said operator to said computer means; and display means coupled to said computer means for displaying said output data from said computer means to said operator.

8. The apparatus of claim 7 wherein said operator interface means further comprising printer means for printing said output data from said computer means.

9. The apparatus of claim 7 wherein said operator interface means further comprising operator panel means having knobs and switches for selecting one of a plurality of detection thresholds for said optical inspection assembly.

10. The apparatus of claim 7 including means for permitting said operator to select one of a plurality of detection thresholds for said optical inspection assembly via said keyboard means.

11. The apparatus of claim 2 wherein said automatic disk handler means comprising, in combination:

at least one input tray wherein said transparent disk is placed prior to inspection by said apparatus;

at least one movable gripper hand located in proximity to said input tray for gripping and transporting said transparent disk from said input tray to said optical inspection assembly;

a first output tray located in proximity to said movable gripper hand such that said transparent disk is moved from said optical inspection assembly to said first output tray by said movable gripper hand if said output of said optical inspection assembly signals to said computer means that said transparent disk has no defects; and a second output tray located in proximity to said movable gripper hand such that said transparent disk is moved from said optical inspection assembly to said second output tray by said movable gripper hand if said output of said optical inspection assembly signals to said computer means that said transparent disk has defects.

12. The apparatus of claim 1 wherein said optical inspection assembly comprising, in combination:

disk movement actuator means in physical proximity to said inspection means for moving said transparent disk to allow said inspection means to fully inspect said transparent disk for defects; and disk movement driver means electrically coupled to said disk movement actuator means and to said computer means for allowing said computer means to control said disk movement actuator means by providing appropriate commands to said disk movement driver means.

13. The apparatus of claim 12 wherein said inspection means comprises surface inspection assembly means for inspecting at least one flat surface of said transparent disk for defects while said disk movement actuator means moves said unit under test.

14. The apparatus of claim 13 wherein said inspection means further comprises edge inspection assembly means in physical proximity to said surface inspection assembly means for inspecting at least one edge of said transparent disk for defects while said disk movement actuator means moves said transparent disk.

15. The apparatus of claim 14 wherein said edge inspection assembly means comprising, in combination:

an outer radius inspection assembly for inspecting at least one outer edge of said transparent disk; and an inner radius inspection assembly for inspecting at least one inner edge of said transparent disk.

16. The apparatus of claim 15 wherein said outer radius inspection assembly and said inner radius inspection assembly perform their respective inspections simultaneously.

17. The apparatus of claim 15 wherein said outer radius inspection assembly comprising, in combination:

a light source;

power supply means electrically coupled to said light source for providing power to said light source;

projection means optically coupled to said light source for projecting said light source onto at least one outer edge of said transparent disk, thereby creating an illuminated portion; and at least one detection means for monitoring said illuminated portion, having output means for reporting the existence of defects in said illuminated portion.

18. The apparatus of claim 17 wherein said detection means further comprising:

a linear array of optical detectors; and detection optics means for directing and projecting an image of said illuminated portion to said linear array.

19. The apparatus of claim 18 wherein said optical detectors comprising Charge-Coupled Devices (CCDs).

20. The apparatus of claim 17 wherein said projection means providing illumination to at least one inner edge of said transparent disk due to light from said light source passing from said outer edge through the transparent media of said transparent disk to said inner edge, thereby illuminating said inner edge.

21. The apparatus of claim 15 wherein said inner radius inspection assembly comprising at least one detection means for monitoring at least one inner edge of said transparent disk, having output means for reporting the existence of defects on said inner edge of said transparent disk.

22. The apparatus of claim 21 wherein said detection means further comprising:

a linear array of optical detectors; and detection optics means for directing and projecting an image of a portion of said inner edge to said linear array.

23. The apparatus of claim 22 wherein said optical detectors comprising Charge-Coupled Devices (CCDs).

24. The apparatus of claim 12 wherein said transparent disk comprising a round disk having an outer edge and a hole in a center portion and wherein said disk movement actuator means comprising at least one actuated roller and motor means for driving said actuated roller for turning said round disk.

25. The apparatus of claim 24 wherein said disk movement actuator means further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

26. The apparatus of claim 25 wherein said actuated roller and said idler roller both having notch means in their circumferential faces in which said outer edge of said round disk is placed for preventing said round disk from slipping off said actuated roller and said idler roller during rotation.

27. The apparatus of claim 13 wherein said surface inspection assembly means comprising, in combination:
  a light source providing said a light beam;
  optical scanner means having an aperture in physical proximity to said light source for permitting said light beam to contact said aperture on said optical scanner means and for reflecting said light beam thereby providing a linear sweep of said light beam;
  scanning optics means having a front face portion and a rear face portion for permitting said linear sweep of said light beam to contact said front face portion of said scanning optics means for causing said light beam that contacts said front face portion to exit said rear face portion and to contact said flat surface of said transparent disk;
  trigger detector means coupled to said computer means and placed within said linear sweep of said light beam for providing a synchronizing electrical signal to said computer means for indicating a position of said light beam along said linear sweep;
  detection optics means having a front face portion and a rear face portion for permitting said light beam after contacting and passing through, said transparent disk to contact said rear face portion and exit said front face portion; and
  said detector means for permitting said light beam exiting said front face portion of said detection optics means to be received by said detector means for detecting changes of a nominal Gaussian distribution of said light beam, said changes corresponding to and identifying defects in said flat surface of said transparent disk.

28. The apparatus of claim 27 wherein said light source comprising a laser diode and said light beam comprising a laser beam from said laser diode.

29. The apparatus of claim 27 wherein said light source comprising a helium-neon laser, and said light beam comprising a laser beam from said helium-neon laser.

30. The apparatus of claim 27 wherein said optical scanner means having a motor-driven polygonal head coupled to said computer means and having reflective faces such that said light beam contacts said reflective faces of said polygonal head through said aperture, and having means for rotating said polygonal head for causing said light beam reflected off said reflective faces to create said linear sweep of said light beam across said scanning optics means.

31. The apparatus of claim 30 wherein said motor-driven polygonal head is turned on and off by said computer means.

32. The apparatus of claim 27 wherein said aperture of said optical scanner means being located at a distance from said scanning optics means equal to the focal length of said scanning optics means.

33. The apparatus of claim 32 wherein said scanning optics means direct said light beam entering said front face portion such that said light beam exits said rear face portion in a direction normal to the focal plane of said scanning optics means.

34. The apparatus of claim 27 wherein said scanning optics means focus said light beam on said flat surface of said transparent disk.

35. The apparatus of claim 27 wherein said trigger detector means comprising an optical sensor having an electrical output corresponding to the presence of said light beam on said optical sensor which is coupled to said computer means.

36. The apparatus of claim 35 wherein said optical sensor comprising a photodiode.

37. The apparatus of claim 35 wherein said optical sensor comprising a charge-coupled device (CCD).

38. The apparatus of claim 27 wherein said detector means comprising, in combination:
  at least two optical detectors having electrical outputs, said optical detectors functioning in parallel; and
  electronic circuitry means for processing said electrical outputs of said optical detectors and generating an electrical signal to said computer means comprising, in combination:
    first input means coupled to said electrical outputs of said optical detectors for monitoring said electrical outputs;
    second input means coupled to said computer means for receiving a threshold value from said computer means;
    processing means coupled to said first input means and to said second input means for measuring said electrical outputs of said optical detectors and for determining the existence of changes of said nominal Gaussian distribution of said light beam above said threshold value on said second input means; and
    output means coupled to said computer means for signaling an occurrence of a change above said threshold value to said computer means.

39. The apparatus of claim 38 wherein said optical detectors comprise photodiodes.

40. The apparatus of claim 38 wherein said optical detectors comprise charge-coupled devices (CCDs).

41. The apparatus of claim 38 wherein said optical detectors are arranged in rows and columns to form a substantially square matrix.

42. The apparatus of claim 38 wherein said optical detectors are arranged in a series of concentric circular rings.

43. The apparatus of claim 27 further comprising filter optics means for increasing spatial coherence of said light beam.

44. A method for inspecting a flat, transparent disk using an optical inspection apparatus including the steps of:
  providing computer means for controlling said apparatus;
  providing operator interface means coupled to said computer means for providing input data from an operator to said computer means and for providing output data from said computer means to said operator;
  providing an optical inspection assembly, coupled to said computer means having output means for reporting to said computer means results of an inspection performed by said optical inspection assembly, comprising inspection means consisting of detector means for detecting changes of a nominal Gaussian distribution of a light beam passing through a transparent disk; and providing said transparent disk which is placed in said optical inspection assembly to inspect said transparent disk for defects.

45. The method of claim 44 further comprising the step of providing automatic disk handler means coupled to said computer means for loading under control of said computer means said transparent disk into said optical inspection assembly and for unloading under control of said computer means said transparent disk out of said optical inspection assembly.

46. The method of claim 44 wherein said computer means comprising, in combination:
    an IBM compatible personal computer; and
    control software means loaded into memory of said IBM compatible personal computer for determining function and sequence of operations of said apparatus.

47. The method of claim 44 wherein said computer means periodically polls said output means of said optical inspection assembly to determine whether a defect has been detected by said optical inspection assembly.

48. The method of claim 44 wherein said output means of said optical inspection means is coupled to said computer means such that said output means interrupts said computer means when a defect is detected by said optical inspection assembly.

49. The method of claim 44 wherein said operator interface means comprising, in combination:
    keyboard means coupled to said computer means for providing said input data from said operator to said computer means; and
    display means coupled to said computer means for displaying said output data from said computer means to said operator.

50. The method of claim 49 wherein said operator interface means further comprising operator panel means having knobs and switches for selecting one of a plurality of detection thresholds for said optical inspection assembly.

51. The method of claim 49 including means for permitting said operator to select one of a plurality of detection thresholds for said optical inspection assembly via said keyboard means.

52. The method of claim 45 wherein said automatic disk handler means comprising, in combination:
    at least one input tray wherein said transparent disk is placed prior to inspection by said apparatus;
    at least one movable gripper hand located in proximity to said input tray for gripping and transporting said transparent disk from said input tray to said optical inspection assembly;
    a first output tray located in proximity to said movable gripper hand such that said transparent disk is moved from said optical inspection assembly to said first output tray by said movable gripper hand if said output of said optical inspection assembly signals to said computer means that said transparent disk has no defects; and
    a second output tray located in proximity to said movable gripper hand such that said transparent disk is moved from said optical inspection assembly to said second output tray by said movable gripper hand if said output of said optical inspection assembly signals to said computer means that said transparent disk has defects.

53. The method of claim 44 wherein said optical inspection assembly comprising, in combination:
    disk movement actuator means in physical proximity to said inspection means for moving said transparent disk to allow said inspection means to fully inspect said transparent disk for defects; and
    disk movement driver means electrically coupled to said disk movement actuator means and to said computer means for allowing said computer means to control said disk movement actuator means by providing appropriate commands to said disk movement driver means.

54. The method of claim 53 wherein said inspection means comprises surface inspection assembly means for inspecting at least one flat surface of said transparent disk for defects while said disk movement actuator means moves said transparent disk.

55. The method of claim 54 wherein said inspection means further comprises edge inspection assembly means in physical proximity to said surface inspection assembly means for inspecting at least one edge of said transparent disk for defects while said disk movement actuator means moves said transparent disk.

56. The method of claim 52 wherein said transparent disk comprising a round disk having an outer edge and a hole in a center portion and wherein said disk movement actuator means comprising at least one actuated roller and motor means for driving said actuated roller for turning said round disk.

57. The method of claim 56 wherein said disk movement actuator means further comprising at least one idler roller, said idler roller and said actuated roller contact said outer edge of said round disk, said actuated roller rotating in response, to said motor means driving said actuated roller causing rotation of said round disk, said rotation of said disk causing said idler roller to rotate.

58. The method of claim 57 wherein said actuated roller and said idler roller both having notch means in their circumferential faces in which said outer edge of said round disk is placed for preventing said round disk from slipping off said actuated roller and said idler roller during rotation.

59. The method of claim 54 wherein said surface inspection assembly means comprising, in combination:
    a light source providing said light beam;
    optical scanner means having an aperture in physical proximity to said light source for permitting said light beam to contact said aperture on said optical scanner means and for reflecting said light beam thereby providing a linear sweep of said light beam;
    scanning optics means having a front face portion and a rear face portion for permitting said linear sweep of said light beam to contact said front face portion of said scanning optics means for causing said light beam that contacts said front face portion to exit said rear face portion and to contact said flat surface of said transparent disk;
    trigger detector means coupled to said computer means and placed within said linear sweep of said light beam for providing a synchronizing electrical signal to said computer means for indicating a position of said light beam along said linear sweep;
    detection optics means having a front face portion and a rear face portion for permitting said light beam after contacting and passing through, said transparent disk to contact said rear face portion and exit said front face portion; and
    said detector means for permitting said light beam exiting said front face portion of said detection optics means to be received by said detector means for detecting changes of a nominal Gaussian distribution of said light beam, said changes corresponding to and identifying defects in said flat surface of said transparent disk.

60. The method of claim 59 wherein said optical scanner means having a motor-driven polygonal head coupled to said computer means and having reflective faces such that said light beam contacts said reflective faces of said polygonal head through said aperture, and having means for rotating said polygonal head for causing said light beam reflected off said reflective faces to create said linear sweep of said light beam across said scanning optics means.

61. The method of claim 60 wherein said motor-driven polygonal head is turned on and off by said computer means.

62. The method of claim 59 wherein said optical scanner means being located at a distance from said scanning optics means equal to the focal length of said scanning optics means.

63. The method of claim 62 wherein said scanning optics means direct said light beam entering said front face portion such that said light beam exits said rear face portion in a direction normal to the focal plane of said scanning optics means.

64. The method of claim 59 wherein said scanning optics means focus said light beam on said flat surface of said transparent disk.

65. The method of claim 59 wherein said trigger detector means comprising an optical sensor having an electrical output corresponding to the presence of said light beam on said optical sensor which is coupled to said computer means.

66. The method of claim 59 wherein said detector means comprising, in combination:
   at least two optical detectors having electrical outputs, said optical detectors functioning in parallel; and
   electronic circuitry means for processing said electrical outputs of said optical detectors and generating an electrical signal to said computer means comprising, in combination:
      first input means coupled to said electrical outputs of said optical detectors for monitoring said electrical outputs;
      second input means coupled to said computer means for receiving a threshold value from said computer means;
      processing means coupled to said first input means and to said second input means for measuring said electrical outputs of said optical detectors and for determining the existence of changes of said nominal Gaussian distribution of said light beam above said threshold value on said second input means; and
      output means coupled to said computer means for signaling an occurrence of a change above said threshold value to said computer means.

67. The method of claim 66 wherein said optical detectors are arranged in rows and columns to form a substantially square matrix.

68. The method of claim 66 wherein said optical detectors are arranged in a series of concentric circular rings.

69. The method of claim 53 further comprising the steps of:
   loading said transparent disk into said disk movement actuator means in said optical inspection assembly;
   activating said surface inspection assembly means with said computer means;
   said computer means providing commands to said disk movement driver means, thereby causing said disk movement actuator means to rotate said transparent disk such that the entirety of said flat surface is inspected;
   checking with said computer means said output of said optical inspection assembly to determine whether a defect was detected by said optical inspection assembly; and
   unloading said transparent disk from said optical inspection assembly into a first destination if said output on said optical inspection assembly did not indicate the presence of a defect on said transparent disk, and unloading said transparent disk from said optical inspection assembly into a second destination if said output of said optical inspection assembly did indicate the presence of a defect on said transparent disk.

70. An apparatus for optically scanning the flat portions of a transparent disk comprising, in combination:
   a light source providing a light beam;
   light beam reflecting means for reflecting said light beam for providing a linear sweep of said light beam;
   a transparent disk having a flat surface to be inspected positioned in said linear sweep of said light beam;
   detector means for receiving said light beam after it has passed through said transparent disk and for detecting changes of a nominal Gaussian distribution of said light beam corresponding to defects in said flat surface of said transparent disk; and
   means for moving said transparent disk within said linear sweep of said light beam and for permitting a linear scan of said flat surface for complete scanning of all of said flat surface to be inspected.

71. The apparatus of claim 70 wherein said light source comprising a laser diode and said light beam comprising a laser beam from said laser diode.

72. The apparatus of claim 70 wherein said light source comprising a helium-neon laser, and said light beam comprising a laser beam from said helium-neon laser.

73. The apparatus of claim 70 wherein said light beam reflecting means comprising an optical scanner.

74. The apparatus of claim 73 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

75. The apparatus of claim 70 wherein said transparent disk comprising a round disk having an outer edge and a hole in a center portion and wherein said means for moving said transparent disk comprising at least one actuated roller and motor means for driving said actuated roller for turning said round disk.

76. The apparatus of claim 75 wherein said means for moving said transparent disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

77. The apparatus of claim 76 wherein said actuated roller and said idler roller both having notch means in their circumferential faces in which said outer edge of said round disk is placed for preventing said round disk from slipping off said actuated roller and said idler roller during rotation.

78. A method for optically scanning the flat surface of a transparent disk comprising, in combination:
   providing a light source having a light beam;
   providing light beam reflecting means for reflecting said light beam for providing a linear sweep of said light beam;
   providing a transparent disk having a flat surface to be inspected positioned in said linear sweep of said light beam;

providing detector means for receiving said light beam after it has passed through said transparent disk and for detecting changes of a nominal Gaussian distribution of said light beam corresponding to defects in said flat surface of said transparent disk; and providing means for moving said transparent disk within said linear sweep of said light beam and for permitting a linear scan of said flat surface for complete scanning of all of said flat surface to be inspected.

79. The method of claim 78 wherein said light beam reflecting means comprising an optical scanner.

80. The method of claim 79 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

81. The method of claim 78 wherein said means for moving said transparent disk comprising at least one actuated roller and motor means for driving said actuated roller for turning said transparent disk.

82. The method of claim 81 wherein said means for moving said transparent disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

83. The method of claim 82 wherein said actuated roller and said idler roller both having notch means in their circumferential faces in which said outer edge of said round disk is placed for preventing said round disk from slipping off said actuated roller and said idler roller during rotation.

84. The method of claim 78 further comprising the steps of:

placing said transparent disk into said means for moving said transparent disk; and activating said means for moving said transparent disk causing all of said flat surface to pass through said linear sweep of said light beam.

85. An apparatus for detecting surface defects in the flat surface of a transparent disk comprising, in combination:

a light source providing a light beam;

light beam reflecting means for reflecting said light beam for providing a linear sweep of said light beam;

a transparent disk having a flat surface to be inspected positioned in said linear sweep of said light beam;

means for moving said transparent disk within said linear sweep of said light beam and for permitting a linear scan of said flat surface for complete scanning of all of said flat surface to be inspected; and detector means for measuring changes in said light beam corresponding to defects on said flat surface of said transparent disk, wherein said detector means receives said light beam after it has passed through said transparent disk and detects changes of a nominal Gaussian distribution of said light beam, said changes corresponding to defects in said flat surface of said transparent disk.

86. The apparatus of claim 85 wherein said light source comprising a laser diode and said light beam comprising a laser beam from said laser diode.

87. The apparatus of claim 85 wherein said light source comprising a helium-neon laser, and said light beam comprising a laser beam from said helium-neon laser.

88. The apparatus of claim 85 wherein said light beam reflecting means comprising an optical scanner.

89. The apparatus of claim 88 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

90. The apparatus of claim 85 wherein said transparent disk comprising a round disk having an outer edge and a hole in a center portion and wherein said means for moving said transparent disk comprising at least one actuated roller and motor means for driving said actuated roller for turning said round disk.

91. The apparatus of claim 90 wherein said means for moving said transparent disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

92. The apparatus of claim 91 wherein said actuated roller and said idler roller both having notch means in their circumferential faces in which said outer edge of said round disk is placed for preventing said round disk from slipping off said actuated roller and said idler roller during rotation.

93. The apparatus of claim 85 wherein said detector means comprising, in combination:

at least two optical detectors having electrical outputs, said optical detectors functioning in parallel; and electronic circuitry means for processing said electrical outputs of said optical detectors and generating an electrical signal output in response to changes of a nominal Gaussian distribution of said light beam above a selectable threshold value.

94. A method for detecting surface defects in the flat surface of a transparent disk comprising, in combination:

providing a light source providing a light beam;

providing light beam reflecting means for reflecting said light beam for providing a linear sweep of said light beam;

providing a transparent disk having a flat surface to be inspected positioned in said linear sweep of said light beam;

providing means for moving said transparent disk within said linear sweep of said light beam and for permitting a linear scan of said flat surface for complete scanning of all of said flat surface to be inspected; and providing detector means for measuring changes in said light beam corresponding to defects on said flat surface of said transparent disk, wherein said detector means receives said light beam after it has passed through said transparent disk and detects changes of a nominal Gaussian distribution of said light beam, said changes corresponding to defects in said flat surface of said unit test.

95. The method of claim 94 wherein said light beam reflecting means comprising an optical scanner.

96. The method of claim 95 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

97. The method of claim 94 wherein said transparent disk comprising a round disk having an outer edge and a hole in a center portion and wherein said means for moving said transparent disk comprising at least one actuated roller and motor means for driving said actuated roller for turning said round disk.

98. The method of claim 97 wherein said means for moving said transparent disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

99. The method of claim 98 wherein said actuated roller and said idler roller both having notch means in their circumferential faces in which said outer edge of said round disk is placed for preventing said round disk from slipping off said actuated roller and said idler roller during rotation.

100. The method of claim 94 wherein said detector means comprising, in combination:

at least two optical detectors having electrical outputs, said optical detectors functioning in parallel; and electronic circuitry means for processing said electrical outputs of said optical detectors and generating an electrical signal output in response to changes of a nominal Gaussian distribution of said light beam above a selectable threshold value.

101. The method of claim 94 further comprising the steps of:

placing said transparent disk into said means for moving said transparent disk;

activating said means for moving said transparent disk causing all of said flat surface to pass through said linear sweep of said light beam; and activating said detector means.

* * * * *